US008905928B2

(12) United States Patent
Hayes et al.

(10) Patent No.: US 8,905,928 B2
(45) Date of Patent: Dec. 9, 2014

(54) METHOD AND APPARATUS FOR ASSESSMENT OF SLEEP DISORDERS

(75) Inventors: Tamara Hayes, Portland, OR (US); Zachary Beattie, Hillsboro, OR (US); Chad Hagen, Portland, OR (US); Misha Pavel, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 111 days.

(21) Appl. No.: 13/384,386

(22) PCT Filed: Jul. 16, 2010

(86) PCT No.: PCT/US2010/042342
§ 371 (c)(1),
(2), (4) Date: Jan. 17, 2012

(87) PCT Pub. No.: WO2011/009085
PCT Pub. Date: Jan. 20, 2011

(65) Prior Publication Data
US 2012/0116187 A1 May 10, 2012

Related U.S. Application Data

(60) Provisional application No. 61/226,483, filed on Jul. 17, 2009.

(51) Int. Cl.
*G06F 19/00* (2011.01)
*A61B 5/00* (2006.01)
*A61B 5/11* (2006.01)
*A61B 5/08* (2006.01)
*A61B 5/024* (2006.01)
*A61B 5/113* (2006.01)

(52) U.S. Cl.
CPC .............. *A61B 5/11* (2013.01); *A61B 5/7264* (2013.01); *A61B 5/0826* (2013.01); *G06F 19/345* (2013.01); *A61B 5/4818* (2013.01); *A61B 5/4812* (2013.01); *A61B 5/6887* (2013.01); *A61B 5/024* (2013.01); *A61B 5/0816* (2013.01); *A61B 5/1102* (2013.01); *A61B 5/113* (2013.01); *A61B 5/6891* (2013.01); *A61B 5/7267* (2013.01)
USPC ............................................. 600/301; 600/300

(58) Field of Classification Search
None
See application file for complete search history.

(56) References Cited

U.S. PATENT DOCUMENTS

| 5,964,720 | A | 10/1999 | Pelz |
| 6,822,571 | B2 * | 11/2004 | Conway ............... 340/573.1 |

(Continued)

FOREIGN PATENT DOCUMENTS

| WO | WO 2008096307 A1 * | 8/2008 | ............ A61M 21/02 |
| WO | WO 2009108228 A1 * | 9/2009 | ............ A61M 21/02 |

OTHER PUBLICATIONS

Brink, Mark et al., "Contact-Free Measurement of Heart Rate, Respiration Rate, and Body Movements During Sleep," Behavior Research Methods, 2006, vol. 38, No. 3, pp. 511-521.

(Continued)

*Primary Examiner* — William Thomson
*Assistant Examiner* — Davin Sands
(74) *Attorney, Agent, or Firm* — Schwabe, Williamson & Wyatt (57) ABSTRACT

Embodiments provide systems, methods and apparatuses for monitoring the sleep of a subject in a home environment. In embodiments, load cells placed under bed supports may be coupled to a computing device that may process the load cell data to detect disordered breathing. In some embodiments, a computing device may apply a pattern recognition algorithm to load cell data to distinguish between normal movements and movements associated with a sleep disorder. In an embodiment, apparatuses and methods for monitoring sleep may perform functions associated with detection of sleep disturbances and/or identify a sleep disorder.

14 Claims, 6 Drawing Sheets

(56) References Cited

U.S. PATENT DOCUMENTS

| | | | |
|---|---|---|---|
| 6,839,581 B1* | 1/2005 | El-Solh et al. | 600/324 |
| 6,856,829 B2* | 2/2005 | Ohsaki et al. | 600/479 |
| 2003/0114736 A1* | 6/2003 | Reed et al. | 600/300 |
| 2004/0010202 A1 | 1/2004 | Nakatani et al. | |
| 2005/0119711 A1* | 6/2005 | Cho et al. | 607/42 |
| 2006/0175097 A1* | 8/2006 | Pirzada | 177/145 |
| 2006/0241510 A1* | 10/2006 | Halperin et al. | 600/534 |
| 2007/0161917 A1* | 7/2007 | Ozaki et al. | 600/529 |
| 2007/0191742 A1* | 8/2007 | Park | 600/587 |
| 2008/0177195 A1* | 7/2008 | Armitstead | 600/529 |
| 2008/0275349 A1* | 11/2008 | Halperin et al. | 600/484 |
| 2008/0306396 A1* | 12/2008 | Ariav et al. | 600/527 |
| 2009/0051549 A1* | 2/2009 | Tochigi et al. | 340/573.4 |
| 2009/0177327 A1* | 7/2009 | Turner et al. | 700/275 |
| 2009/0203972 A1* | 8/2009 | Heneghan et al. | 600/301 |
| 2010/0191136 A1* | 7/2010 | Wolford | 600/534 |

OTHER PUBLICATIONS

Choi, Byoung Hoon et al., "Non-Constraining Sleep/Wake Monitoring System Using Bed Actigraphy," Med Bio Eng. Comput, 2007, vol. 45, pp. 107-114.

Chung, Gih Sung et al., "Noninvasive Heart Rate Variability Analysis Using Loadcell-Installed Bed During Sleep," Proceedings of the 29th Annual International Conference of the IEEE EMBS, Cite Internationale, Lyon, France, Aug. 23-26, 2007, pp. 2357-2360.

Adami, A.M. et al., "Detection and Classification of Movements in Bed Using Load Cells," Proceedings of the 2005 IEEE Engineering in Medicine and Biology 27th Annual Conference, Shanghai, China, Sep. 1-4, 2005, pp. 589-592.

Adami, A.M. et al., "Unobtrusive Monitoring of Sleep Patterns," Proceedings of the 25th Annual International Conference of the IEEE EMBS, Cancun, Mexico, Sep. 17-21, 2003, pp. 1360-1363.

Adami, Adriana M. et al., "A System for Unobtrusive Monitoring of Mobility in Bed," The 11th IEEE International Conference on Computational Science and Engineering Workshops, 2008, pp. 13-17.

Choi, Byung Hun et al., "Slow-wave Sleep Estimation on a Load-Cell-Installed Bed: a Non-Constrained Method," Physiological Measurement, 2009, vol. 30, pp. 1163-1170.

Chung, Gih Sung et al., "Unconstrained Heart Rate Estimation System in Bed," 2007 International Conference on Convergence Information Technology, pp. 2363-2367.

Chung, Gih Sung et al., "REM Sleep Classification with Respiration Rates," 6th International Special Topic Conference of ITAB, 2007, Tokyo, Japan, pp. 194-197.

Shin, J.H. et al., "Automatic Ballistocardiogram (BCG) Beat Detection Using a Template Matching Approach," 30th Annual International IEEE EMBS Conference, Vancouver, BC, Canada, Aug. 20-24, 2008, pp. 1144-1146.

Aubert, Xavier L. et al., "Estimation of Vital Signs in Bed from a Single Unobtrusive Mechanical Sensor: Algorithms and Real-life Evaluation," 30th Annual International IEEE EMBS Conference, Vancouver, British Columbia, Canada, Aug. 20-24, 2008, pp. 4744-4747.

* cited by examiner

METHOD AND APPARATUS FOR ASSESSMENT OF SLEEP DISORDERS

CROSS REFERENCE TO RELATED APPLICATIONS

The present application is a nonprovisional of and claims priority to U.S. Patent Application No. 61/226,483, filed Jul. 17, 2009, entitled "Method and Apparatus for Assessment of Sleep Disorders," the entire disclosure of which is hereby incorporated by reference in its entirety.

GOVERNMENT INTERESTS

This invention was made with Government support under Grant/Contract No. 1R01AG024059-01A1 awarded by the National Institutes of Health. The Government has certain rights in the invention.

TECHNICAL FIELD

Embodiments herein relate to the field of sleep disorder monitoring, and, more specifically, to methods and apparatuses for monitoring sleep disturbances.

BACKGROUND

The Institute of Medicine reports that 50 to 70 million Americans suffer from what they refer to as disorders of sleep and wakefulness, including more than 30 million who suffer from sleep apnea. The current standard of care for diagnosing and monitoring these disorders is overnight polysomnography (PSG), a multiparametric test that monitors eye movement, respiratory airflow, blood oxygen saturation, hearth rhythm and other biophysical signs. Unfortunately PSG is expensive, obtrusive, and inconvenient. Patients who are already struggling with sleep are physically wired to several sensors and asked to sleep normally in a sleep lab. Also, these tests are not usually performed frequently enough to detect the night-to-night variance that many sleep disorders exhibit or to track a patient's progress after treatment has been prescribed. Based on a single night of data from a highly disruptive device, a doctor will prescribe treatment. No follow-up of the efficacy of the treatment occurs, although the patient may return to the sleep lab in 4-6 months for another evaluation.

The high cost and obtrusive nature of PSG, the gold standard for studying sleep, makes PSG an impractical tool for monitoring individuals' sleep over several nights. Other less intrusive methods have been developed to detect other movements during sleep, such as respiration. One such method has been to attach a mechanical sensor to a mat that can be placed on top of the bed (Aubert et al. 2008). The technique has high accuracy in detecting heart and respiration rates; however, the mat alters the sleeping surface of the bed and the device must be placed near the thorax of the patient.

Currently, some alternative methods for studying sleep disorders include the detection of Periodic Leg Movements (PLM), a common symptom of disruptive sleep. One popular alternative method is to use accelerometers to measure the actigraphy of leg movements. However, these devices are obtrusive and are limited in both memory and battery capacity. The KickStrip™ is a PLM monitoring device that may be placed on each leg to detect leg movements, but it is also obtrusive and merely counts the gross number of PLM's that occur within a given period of time. In contrast, the static charge sensitive bed is unobtrusive but also sensitive to all movement. As a consequence, this device cannot localize movement to the subject's legs. Portability of the device is also limited because it requires two large metal plates separated by a wood insulator.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

The description may use the terms "bed" and "bed support." The term "bed" may be used to mean any structure with a generally horizontal surface used/intended for use in supporting a body during a period of rest and/or sleep, including (but not limited to) beds, mattresses, futons, couches, bassinets, cribs, cots, cradles, recliners, and other similar structures. "Bed support" may be used to mean any structure that physically supports a "bed" on a surface such as a floor. A bed support may be an integral part of a bed and/or may be a separate component that is added to the bed. A bed may include one, two, three, four, five, six, seven, eight or more bed supports.

The term "load cell" may be used to mean any mechanism that translates/converts force into a signal such as an electrical or analog signal. Load cells/transducers are known in the art, and the description provided herein is intended to embrace all such mechanisms. Load cells in accordance with various embodiments may be coupled to a computing device by a physical connection such as a cable or a wire, and/or may be in wireless communication with a computing device and/or another load cell.

The gold standard for diagnosing sleep problems is overnight polysomnography (PSG), an obtrusive test in which patients spend a night in a sleep lab wired to up to 15 different devices for measuring airflow, movement, and electrical brain signals. However, the test is expensive, inconvenient, and time-consuming, and it interferes with normal sleep patterns. Therefore, embodiments herein provide a simpler, more cost-effective way to triage sleep disorders in the general population. A significantly better understanding of an individual's sleep and changes in their sleep patterns over time may be obtained by monitoring their sleep in a non-invasive manner, preferably in their own home. Furthermore, treatment may be assessed and optimized if data is available on the time course of improvements as a result of the treatment.

Load cells may be used to detect and classify movements in bed and to assess sleep hygiene. In an embodiment, load cells placed under each support of a bed offer a unique opportunity to continuously and unobtrusively monitor patients while they sleep. The patterns of changing pressure at each support may be analyzed and inferences about various sleep parameters may be made. Each pressure signal contains information about the amplitude and variability of the person's heart rate and respiration rate, as well as about the number, timing, and intensity of movements. This information may be extracted from the signal using combined time domain and frequency domain techniques, including but not restricted to Fourier analysis, wavelet analysis, and/or peak detection. In some embodiments this information may be extracted from individual load cells and combined using averaging or voting techniques. In some embodiments the signals from multiple load cells may be used to determine the center of pressure on the bed and the resultant center of pressure signal may itself be used to extract the information. In some embodiments a single load cell correctly tensioned may provide sufficient data to derive the measures of interest, including respiration, heart rate, and movement. Data from the load cells may be collected in a person's home, allowing physicians and researchers the ability to monitor a patient's sleep over time without imposing on the patient or their sleep.

Embodiments described herein provide systems, apparatuses and methods for the monitoring of sleep disorders. Embodiments described herein may be adapted for use in home environments. In some embodiments, a method of monitoring sleep may comprise: collecting data from a load cell, the load cell being positioned below a bed support and the data indicating force exerted against the load cell, the collecting occurring during a period of sleep or rest on the bed; processing the data; extracting a first physiological parameter from the data, the parameter comprising at least one of respiration, body position, PLM, and heart rate; and identifying, based on one or more physiological parameters, a sleep disorder, wherein the collecting, extracting and identifying are performed by a computing device comprising executable instructions for applying a pattern recognition algorithm to the data. In some embodiments, a sleep disorder may include sleep disordered breathing and/or one or more sleep movement disorders. A sleep movement disorder may include PLM, restless leg syndrome, and/or any abnormal sleep movement.

In some embodiments of the above method, the processing may comprise at least one of decimating the data, filtering the data, and segmenting the data into periods of movement and stillness. In an embodiment, the extracting may further include extracting one or more additional physiological parameters from the data, and the identifying may be based on the one or more physiological parameters. For example, one, two, three, four, five, six or more physiological parameters may be extracted from the data and a sleep disorder may be identified based on one or more of the extracted physiological parameters. In some embodiments of the above method, the processing may include windowing the signal into short overlapping time segments, and extracting the physiological parameters from each window, using estimates of the parameters from prior windows to adaptively update the estimate for the current window. In some embodiments, one or more additional physiological parameters may be extracted from the physiological parameters extracted from the data. For example, 2-6 parameters extracted from the data may be combined and additional parameters may be extracted from the combined 2-6 parameters. The first physiological parameter may be extracted from data representing periods of stillness—for example, where the first physiological parameter is heart rate or respiration, the heart rate or respiration may be extracted from data representing periods during which the monitored subject does not otherwise move. Alternatively, the first physiological parameter may be extracted from data representing periods of movement. In some embodiments, collection of data and/or another step may be performed substantially continuously for a period of time.

Embodiments herein described provide apparatuses for monitoring sleep. An apparatus in accordance with various embodiments may comprise: a load cell configured for placement below a bed support, the load cell further configured to convert force to a signal (such as an electrical signal) indicative of the force; and a computing device coupled to the load cell, the computing device comprising computer executable instructions for receiving signals from the load cell, processing the signals, extracting a physiological feature from the signal data, and identifying an incident of a sleep disorder, which includes but is not limited to obstructive sleep apnea, central sleep apnea, Cheyne Stokes breathing, Periodic Leg Movements in Sleep, and Restless Leg Movements. The computer executable instructions may comprise a pattern recognition algorithm. In some embodiments, an apparatus for monitoring sleep may further include a transceiver coupled to at least one of the computing device and the load cell. In an embodiment further comprising an alarm, the computer executable instructions may be operable to actuate the alarm in response to identifying an incident of abnormal respiration.

In embodiments, one or more load cells may be placed beneath supports of a bed to unobtrusively monitor subjects while they sleep. Patterns of changing pressure at each support may be analyzed and inferences about various sleep parameters may be made. Data from the load cells may be collected in a person's home, and collected data may be processed to extract information about the person's respiration, heart rate, PLM, and/or other physiological parameters. Such information may be used in the diagnosis of a sleep disorder and/or to monitor a sleep disorder or an associated treatment. Systems in accordance with embodiments may also be used by physicians and/or others to monitor a patient's/subject's sleep in hospitals, laboratories, and/or health facilities. Systems and methods may also be used to monitor sleep over time without imposing on the subject's sleep.

Figure 1:
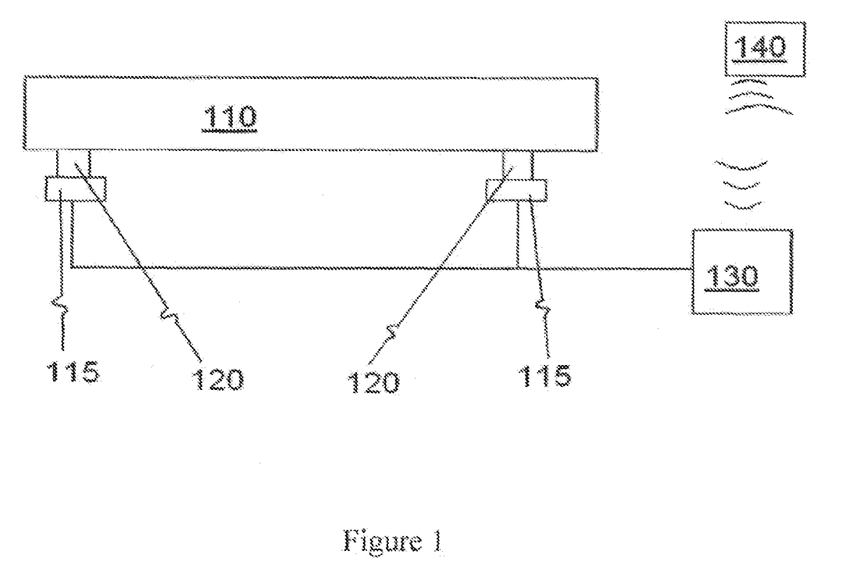
FIG. 1 illustrates a block diagram of an apparatus for monitoring sleep disorders in accordance with various embodiments.

FIG. 1 illustrates a block diagram of an apparatus for monitoring sleep disorders in accordance with various embodiments. In embodiments, a bed 110 may be coupled to bed supports 120 such that the bed is physically supported by the bed supports. Load cells 115 may be positioned beneath the bed supports 120 such that the bed and bed supports are physically supported by the load cells. While two cells are shown in FIG. 1, embodiments may vary as to the number of load cells used. In some embodiments, a load cell may be placed under each corner/support of a bed and/or under one or more other bed supports. In some embodiments an additional load cell may be attached to a new support that is placed under the bed and correctly tensioned to provide support and measure the load at a specific location. The load cells 115 may be coupled to a computing device 130 comprising executable instructions for collecting data from load cells, processing the data, extracting features from the data, and detecting a sleep disorder and/or a movement associated with a sleep disorder. The computing device 130 may be in communication with an external computing device 140. Load cells 115, computing device 130 and external computing device 140 may be coupled with a physical connection such as a cable and/or wirelessly coupled, and/or may communicate with one another by means of telephony and/or telemetry.

In embodiments, a computing device 130 may be adapted to send data to external computing device 140 to communicate information about a subject's sleep. Computing device 130 may include a personal computer, a handheld computing device, a wireless communication device, or any computing apparatus known in the art, and may be located near the bed or in another location. External computing device 140 may be a computing device located in another device such as a medical office, hospital, caretaker's residence, laboratory, etc. One or both of computing device 130 and/or external computing device 140 may be equipped with an alarm and logic to activate an alarm in response to an indication of a sleep disturbance/abnormal movement.

Systems and methods in accordance with various embodiments may provide for the detection of sleep disturbances by a computing device programmed with executable code operable to process signals from load cells coupled to the computing device. In some methods, one or more steps may be performed automatically by a computing device. In an embodiment, all steps of a method may be performed automatically by a computing device. Processing of signals may include filtering and/or decimating a portion of load cell signal data. In embodiments, one or more algorithms may be applied to signal data (and/or to data produced by signal data processing) to identify/differentiate between movements during sleep that are associated with respiration, PLM, and/or cardiac activity of a subject.

Figure 2:
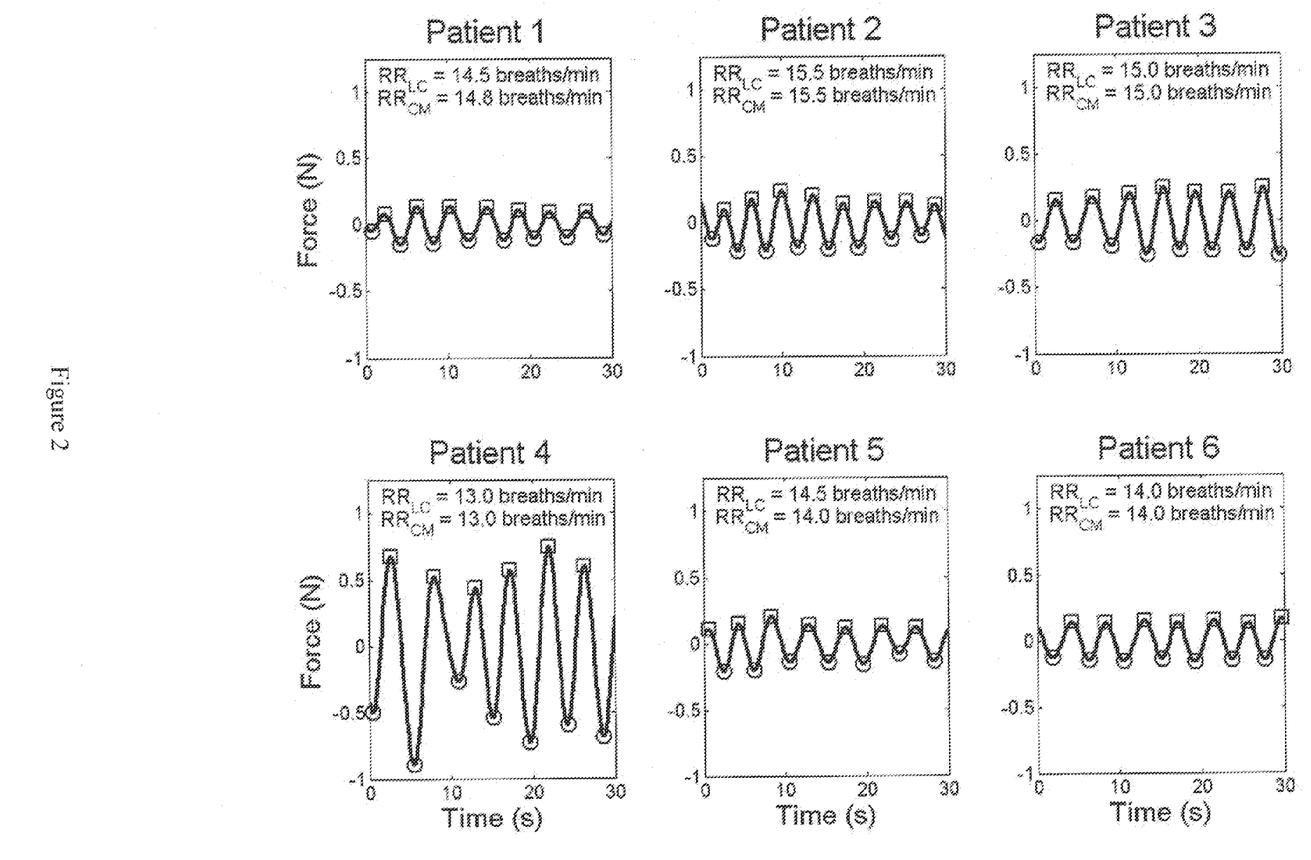
FIG. 2 illustrates detected respiration peaks and troughs in filtered load cell signals collected from 6 patients during overnight sleep studies.

In some embodiments, the load cell signal may be filtered to eliminate all other frequencies except those associated with the respiration signal. As an example, FIG. 2 contains several segments where the load cell signals have been frequency filtered to only contain the respiratory signal. The respiration rate was calculated by detecting the respiration peaks in the filtered load cell signal and by determining how many peaks were present in a known time period. The respiration rate calculated in this manner, $RR_{LC}$, was comparable to the clinical estimate of respiration, $RR_{CM}$.

Figure 3:
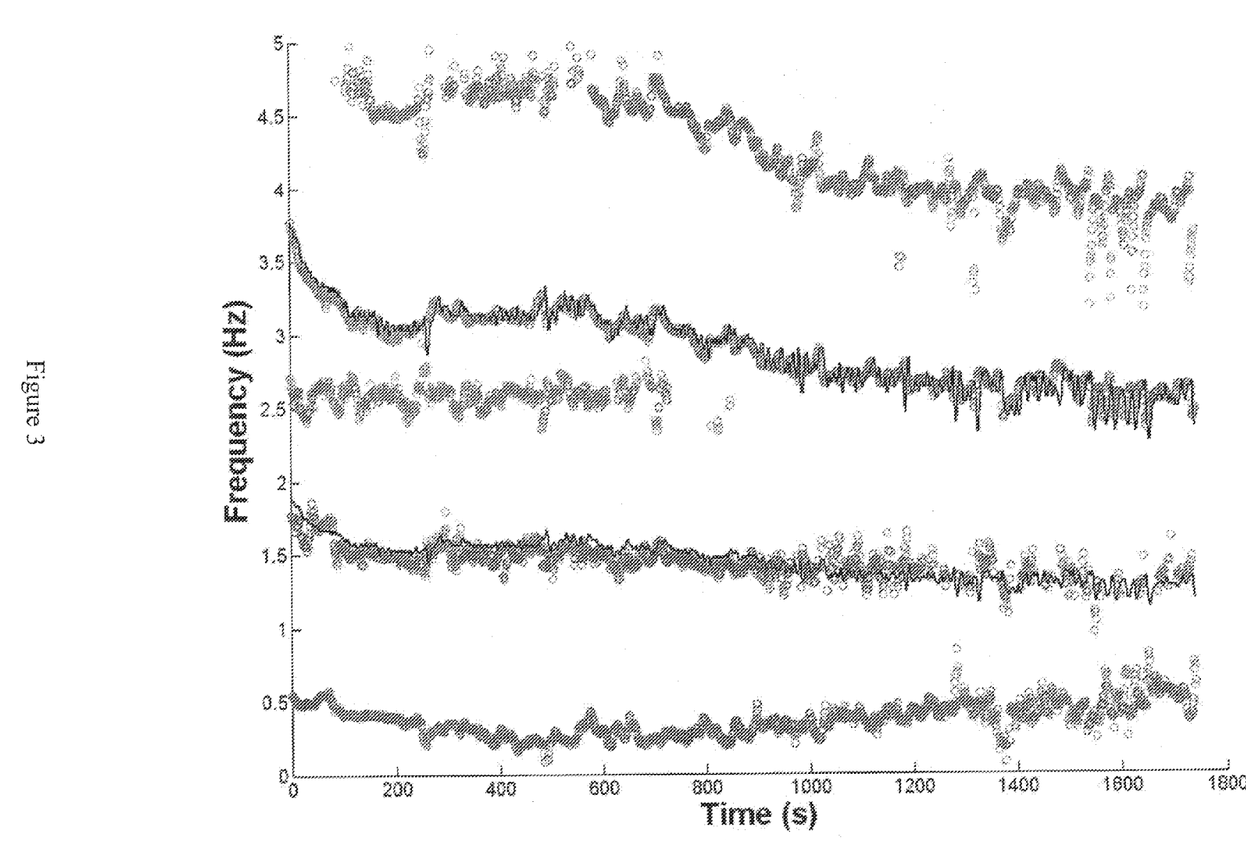
FIG. 3 illustrates frequency in a load cell signal over time and estimated pulse rate frequencies.

In another embodiment, the cardiac activity may be extracted from the load cell signal using the frequency content of the signal. FIG. 3 contains an example where the frequency content of a load cell signal is shown to be associated with the heart rate frequencies that were estimated using the pulse rate as calculated by a pulse oximeter. In FIG. 3, the fundamental pulse rate frequency (lower black trace) was estimated by dividing the pulse rate by 60, and the first harmonic of the pulse rate frequency (upper black trace) was estimated by dividing the pulse rate by 30.

In embodiments, the variance of the load cell signal may be used to detect other movements during sleep that are not associated with the breathing or cardiac activity of the subject. Regions of movement will have greater variance than regions of non-movement. In some embodiments, these movements could be used to detect large body movements in order to segregate the load cell signal into periods of quiescence where the respiration and cardiac movements are detectable. In other embodiments, periodic movements may be used to detect periodic leg movements or PLMs. One or more algorithms may also be applied to processed/unprocessed signal data to identify and/or distinguish between sleep parameters such as periods of central apnea, obstructive apnea, mixed apnea (comprising both central and obstructive apnea), and/or hypopnea.

In some embodiments, one or more signal processing techniques may be used to differentiate between central apnea, obstructive apnea, mixed apnea and/or hypopnea. One or more statistical pattern classification techniques may be used to differentiate between different movement types, such as differentiating between PLMs, restless leg movements, normal leg motion, and normal limb motion. Additional algorithms may be used to extract parameters of respiration, cardiac activity, and/or motion associated with a stage of sleep. In some embodiments of the above methods, the processing may include windowing the signal into short overlapping time segments and extracting physiological parameters from each window which may include but are not limited to the amplitude of the respiration signal, the variance of the respiration and cardiac signal, and the amount of variance in the detected movements that are not associated with the breathing or cardiac signal such as body or limb movements. These physiological parameters may be used to distinguish which class of breathing, class of body movement, or class of sleep stage the segment represents. In an embodiment, statistical pattern classification may be used to determine the class of breathing, class of body movement, or class of sleep stage by utilizing the probabilities that each physiological parameter belongs to a specific class. In an embodiment, data indicative of motion may be provided periodically and/or continuously to a computing device by a load sensor, and the computing device may integrate the data to detect (and/or to signal the detection of) a pattern of movement associated with a sleep disturbance such as a period of apnea. In an embodiment, the provision/integration/signaling may be performed automatically by one or more computing devices.

Methods of monitoring sleep in a home environment may include collecting data from load sensors and analyzing the collected data to identify and/or categorize movements of the subject during sleep. In an embodiment, a method of monitoring sleep in a home environment may include extracting periods of movement from the data using an algorithm, determining respiration rate from periods of stillness, and identifying periods of apnea and/or hypopnea. A sleep monitoring method may further include differentiating PLMs from other types of movements. In some embodiments, a sleep monitoring method may be performed periodically/automatically by an apparatus comprising one or more load cells coupled to a computing system/device. In some embodiments, a method of monitoring sleep in a home environment may comprise collecting data from load cells placed under supports of a subject's bed, filtering and/or decimating the data, extracting features from the raw and filtered load cell signals, and using the statistical distribution of the features to train a classifier to differentiate between categories of movement based on the probabilities that the features belong to each category. The classifier may be a simple Bayesian classifier in which the parameters of the classifier are approximated using the maximum likelihood probabilities of a training set of data which contains examples of the sleep patterns of interest. In other embodiments the classifier may use any of a number of well-known supervised and unsupervised machine learning techniques such as neural networks or support vector machines. In an embodiment, this method may be used to differentiate normal and disrupted breathing. In some embodiments, a method may be used to differentiate PLM and other types of movements. In some embodiments, a method may be used to differentiate regular from irregular heart rate. In embodiments, performance of a step may trigger performance of another step. One or more steps may be performed by a computing device, while other steps may be performed manually.

Figure 4:
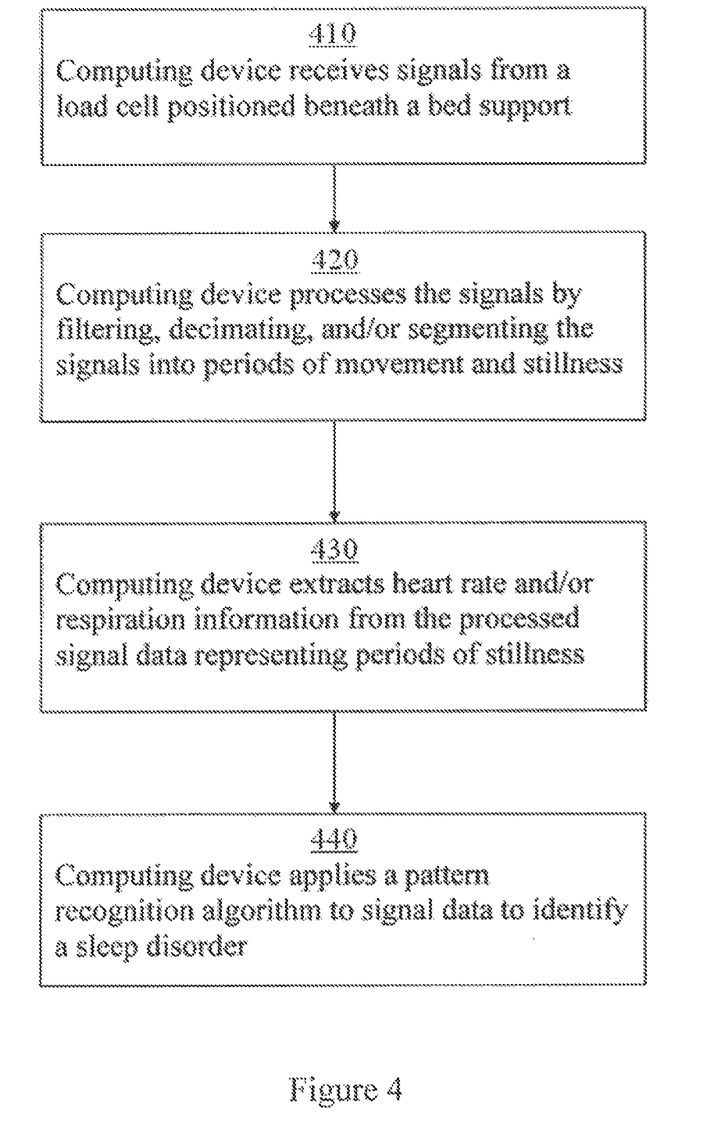
FIG. 4 illustrates a flow chart for a method of monitoring sleep disorders in accordance with various embodiments.

FIG. 4 illustrates a flow chart for a method of monitoring sleep disorders in accordance with various embodiments. In step 410, a computing device receives signals from a load cell positioned beneath a bed support. In step 420, the computing device processes the signals by filtering, decimating, and/or segmenting the signals into periods of movement and stillness. Next, in step 430, the computing device extracts heart rate and/or respiration information from the processed signal data representing periods of stillness. In step 440, the computing device applies a pattern recognition algorithm (such as a statistical pattern recognition algorithm) to signal data to identify a sleep disorder. One or more steps may be performed automatically by a computing device; in some embodiments, each step is performed automatically by a computing device. In embodiments, performance of one step may trigger performance of another step. A step may be performed manually, performed by a computing device, and/or performed automatically.

Figure 5:
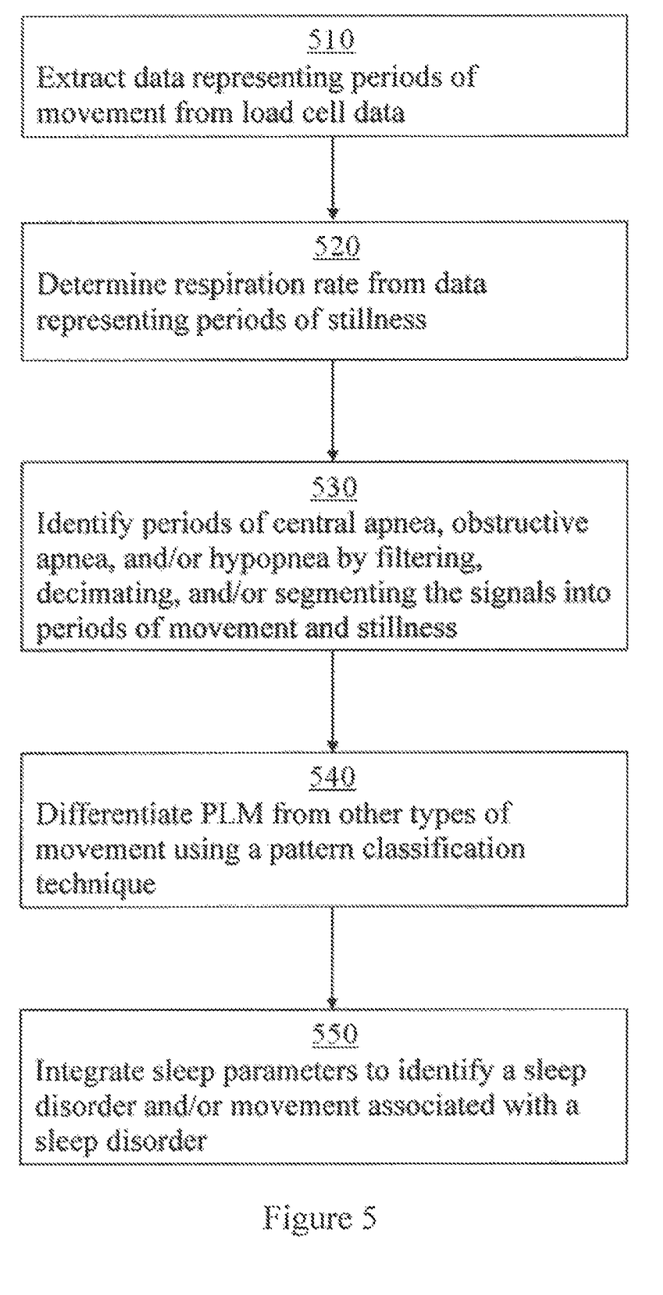
FIG. 5 illustrates a flow chart for a method of identifying a sleep disorder and/or movement associated with a sleep disorder using data from load cells in accordance with various embodiments.

FIG. 5 illustrates a flow chart for a method of identifying a sleep disorder and/or movement associated with a sleep disorder using data from load cells in accordance with various embodiments. The steps of FIG. 5 may be performed automatically by a computing device provided with the appropriate logic. First, in step 510, a computing device may extract data representing periods of movement from load cell data. Next, in step 520, the respiration rate may be determined by the computing device from data representing periods of stillness. In step 530, the computing device may identify periods of central apnea, obstructive apnea, and/or hypopnea by filtering, decimating, and/or segmenting the signals into periods of movement and stillness. In step 540, the computing device may differentiate PLM from other types of movement using a pattern classification technique. In step 550, the computing device may integrate multiple sleep parameters to identify a sleep disorder and/or identify movement associated with a sleep disorder. In various embodiments, methods for monitoring sleep and/or identifying a sleep disorder/movement associated with a sleep disorder may include using a classifier to differentiate normal and abnormal movements of a monitored subject. In some embodiments a Bayesian classifier may be used and/or trained for use for this purpose.

The example discussed below demonstrates the use of load cells to detect disordered respiration during sleep in a home environment, in accordance with various embodiments. In this example, data were collected from load cells placed under beds of subjects to be monitored during sleep. Features were extracted from raw and filtered load cell signals and used to train a Bayesian classifier to differentiate normal and disruptive breathing. Embodiments may vary as to the methods of feature extraction, classifier, and/or classifier training. The example discussed below is for illustrative purposes only and is not intended to be limiting.

Figure 6:
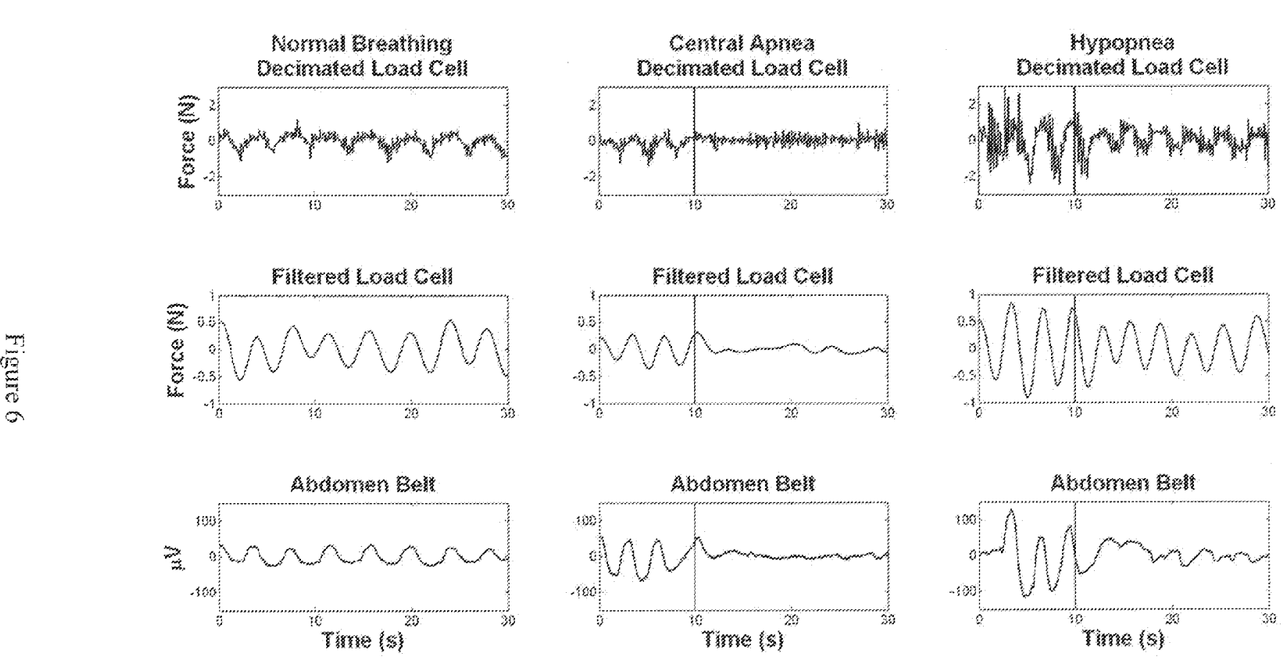
FIG. 6 illustrates graphs of patient data from three different 30 second epochs obtained during a sleep study, using both standard PSG and a method in accordance with various embodiments.

FIG. 6 (described in further detail below) shows patient data from three different 30 second epochs obtained during a sleep study, using both standard PSG and a method in accordance with various embodiments. In the illustrated embodiment, load cells were placed under each support of a bed in the OHSU sleep clinic. Data were collected on four patients admitted for regular polysomnography (PSG) evaluation. Both full polysomnography data and load cell data were collected for each patient and time-aligned for analysis.

The polysomnography data were scored clinically to obtain periods of apnea and hypopnea. The clinically determined times and durations of hypopneas and central apneas were used to segment the load cell data for analysis. Representative samples of hypopneas/obstructive apneas (N=150) and of central apneas (N=150) were segmented from the load cell data. An additional 150 samples of normal breathing that did not contain apneic events were also segmented from the load cell data. The duration of the normal breathing segments was chosen to be the average of the 300 apneic events, 20 seconds.

The entire load cell signal from each load cell, x(t) was low-pass filtered to 5 Hz and then decimated to 10 Hz. It was then further filtered using a $7^{th}$ order low-pass Chebyshev Type II filter to isolate the respiration signal. The low-pass filter had a stop-band edge frequency of 0.45 Hz, was monotonic in the passband, and attenuated the stop-band by 40 dB.

For each load cell i, the signal was separately decimated (down sampled) ($x^i_d(t)$) and filtered as described above ($x^i_{BP}(t)$). These signals were then segmented based on the polysomnography data as described above. FIG. 6 shows sample signals from the PSG, the decimated load cell segment $x^i_d(t)$, and the filtered load cell segment $x^i_{BP}(t)$, for each class of breathing data (normal breathing, central apnea, and hypopnea. The left column depicts an epoch of normal breathing, the middle column depicts a central apnea, and the right column depicts a hypopnea. The upper row contains decimated data from the load cell placed under the upper middle support of the bed. The middle row contains filtered load cell data from the same sensor. The bottom row contains data from the PSG respiratory inductive plethysmography abdomen belt during the 30 second epoch. The vertical line indicates the time point where the respective respiratory event was scored by an OHSU sleep lab technician. This data shows a similar cessation of breathing signal in the load cell as in the abdomen belt during a central apnea. The peak-to-peak amplitude in the load cell signal also decreases during the hypopnea similar to the decrease seen in the abdomen belt signal.

Eight features were extracted from each load cell period k for each load cell i. The index i is dropped for clarity. From the decimated signal segments, $x_d(t)$, various features were extracted.

Variance, $s_k^2$, in the signal over the entire period of each respiratory segment was calculated.

Normalized average power of the signal in the three frequency bands [0-0.5 Hz], [0.6-0.75 Hz], and [0.75-5 Hz]. These measures provided information about the relative frequency content in each of these bands. Normal breathing periods would be expected to have a larger signal in the lower frequency range, corresponding to the stronger respiration signal. To calculate the average power, each signal sample was treated as part of a wide-sense stationary process with non-zero average power. The power spectral density (PSD) of the period, S, was calculated by first multiplying the decimated signal, $x^k_d(t)$, segment by a Blackman window to get the signal $x^k_B(t)$, and then using the normalized and squared absolute value of the Fourier transform on this modified segment:

$$S_k(e^{j\omega}) = \frac{1}{n}\left|\sum_{t=1}^{n} x_B^k(t)e^{-j\omega t}\right|^2$$

The Blackman window reduces the side-lobe amplitude in the estimated spectrum by about 58 dB, and has a roll-off of about 18 dB per octave. The average power, P, in a given frequency band $[F_1, F_2]$ is calculated from the PSD, S, as $$P_{kF_1F_2} = 2\sum_{i=F_1}^{F_2} S_k(f_i).$$

Spectral entropy, SE, of the signal. SE was calculated by finding the PSD of the decimated load cell signal, $x_d(t)$, segmenting the PSD into 100 equal frequency bins, f, normalizing each bin's average power to find its probability density, $p_f$, and using the equation:

$$SE = \sum_{f=1}^{100} p_f \log_{10}\left(\frac{1}{p_f}\right).$$

From the filtered signal segments, $x_{BP}(t)$, the following additional features were extracted:
  Variance, $s^2$, in the signal. Variance was calculated as was done for the decimated signal segments.
  Range, R, of the data values in the period. Range was calculated using the maximum and minimum data values of the filtered signal segment, $x_{BP}(t)$:

$$R = \max(x_{BP}(t)) - \min(x_{BP}(t)).$$

Respiration amplitude, RA. RA was estimated by dividing each segment into overlapping 5 second windows that have starting points offset by 0.1 seconds, finding the range of the data in each window, and then taking the median of all the ranges. A peak detection algorithm to find inspiration peaks and troughs was not utilized in this example because they are not always easily identifiable in disordered breathing, especially in cases of central apneas. However, in some embodiments, a simple peak detection algorithm and/or similar algorithm may be used to find inspiration peaks and/or troughs, by identifying local maxima and minima which represent the peaks and troughs of respiration in a signal filtered to only contain the respiration signal.

To separate the load cell respiratory segments into the three classes, Bayesian learning was used to determine the class-conditional probabilities $P(x|w_i)$ by fitting the features from each class with a multivariate normal density where x is the set of features for a particular respiration segment and $w_i$ represents $i^{th}$ class. Likelihood ratios were used to assign each observation to one of the groups. The performance of the classifier was assessed using 10-fold cross validation. The 150 data segments from each class were divided into 10 disjoint sets of 15 samples. The classifier was trained 10 times, each time with one set of samples held out for validation. The 10-fold cross validation was performed for each load cell, and each load cell was allowed to "vote" for the classification of each true event. The class with the most votes was selected as the predicted class. In the case where more than one class shared the most votes, the class predicted by the load cell under the upper middle of the bed was selected. Finally, the sensitivity and specificity of the classifier were averaged over the ten iterations for each class.

Clinically, the measure most often used to assess sleep disordered breathing is the Apnea-Hypopnea Index (AHI), which does not differentiate between apneas and hypopneas. Therefore, the method described was used to separate the load cell respiratory segments into two classes: periods of disordered breathing (combined data of the hypopneas, obstructive apneas, and central apneas, N=300), and periods of normal breathing (N=150). The average sensitivity and specificity for this classifier were also found using 10-fold cross validation. However, this time the 300 combined data segments for the disordered breathing were divided into 10 disjoint sets of 30 samples that were randomly sampled without replacement. The 150 normal breathing segments were divided as explained above. In some embodiments, other methods of dividing normal/abnormal breathing segments may be used.

Tables 1 and 2 below show the sensitivity and specificity obtained for each type of breathing event in the illustrated example. The specificity was reasonably high in this example for the disordered breathing events (apneas and hypopneas). The confusion matrix shows that hypopneas were primarily confused with normal breathing in this example, although some were confused with central apneas. The feature that best differentiated the hypopneas from other classes was the normalized power in the [0.6-0.75 Hz] frequency band.

TABLE 1

Sensitivity and Specificity for All Classes

| | Sensitivity | Specificity |
| --- | --- | --- |
| Hypopnea/Obstructive Apnea | 0.65 | 0.90 |
| Central Apnea | 0.82 | 0.92 |
| Normal Breathing | 0.84 | 0.84 |

TABLE 2

| | Actual Class | | |
|---|---|---|---|
| | Hypopnea/Obstructive Apnea | Central Apnea | Normal Breathing |
| Estimated Class | | | |
| Hypopnea/Obstructive Apnea | 97 | 15 | 16 |
| Central Apnea | 17 | 123 | 8 |
| Normal Breathing | 36 | 12 | 126 |

Results were better when the disordered breathing events were considered as a single group, as is done clinically when calculating AHI. The sensitivity and specificity for discerning disordered breathing segments was 0.77 and 0.91 respectively, and the sensitivity and specificity for discerning normal breathing segments was 0.91 and 0.77 respectively.

Embodiments of methods, systems and apparatuses for detecting sleep apnea may include various classifiers to separate different types of movement associated with events such as respiration, cardiac activity, PLM, normal movements, and other sleep-related movements. The overall performance of the above classifier in separating normal breathing from disordered breathing was acceptable.

In some embodiments, other classifiers may be used to discriminate hypopneas from apneas. The scoring of apneas and hypopneas in PSG may be scored according to two different rules, as described by the American Academy of Sleep Medicine (AASM) guidelines. Hypopneas are quite distinguishable visually from apneas in the load cell data, and in some embodiments, these breathing events may be classified by a variety of methods. Some embodiments may include features that provide information about the time course of the signal during the event, such as features derived from wavelets.

The above example focuses on the classification of different breathing events from load cell data segmented using the PSG data as a gold standard. In other embodiments, a classifier may include additional features and/or be trained with a larger training set. In some embodiments, quiescent periods may be automatically segmented by type of breathing (central apnea, hypopnea, and normal breathing). This may be used for estimating an apnea-hypopnea index from in-home data. Some embodiments may also include identifying types of movements to the classification and assessment of Periodic Leg Movements, which is another common symptom of disrupted sleep.

The potential of this technology for assessing sleep disorders lies in its unobtrusive nature, and on the fact that it may be used to assess disrupted sleep in a person's own bed. The potential cost savings in a tool that may be used to pre-screen for sleep apnea, or to follow treatment, is significant.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of differentiating between central apnea, hypopnea, and normal breathing during sleep in a subject, the method comprising:
    collecting, by a computing device, load cell signal data from one or more load cells, the load cells being positioned below one or more supports of a bed such that the bed and the one or more bed supports are physically supported by the load cells, the load cell signal data indicating force exerted against the load cell, the collecting being performed while the subject is sleeping;
    decimating, by the computing device, the load cell signal data to obtain downsampled load cell signal data;
    filtering, by the computing device, the load cell signal data to obtain filtered load cell signal data;
    extracting, by the computing device, features from the downsampled load cell signal data;
    extracting, by the computing device, features from the filtered load cell signal data;
    applying, by the computing device, a classifier to the features extracted from the downsampled load cell signal data and the features extracted from the filtered load cell signal data to classify the load cell signal data, the classifier differentiating between central apnea, hypopnea, and normal breathing; and
    identifying, by the computing device, central apnea, hypopnea or normal breathing in the subject based on the classification of the load cell signal data.

2. The method of claim 1, further comprising segmenting, by the computing device, the data into periods of movement and stillness.

3. The method of claim 1, wherein the load cell signal data includes load cell signal data representing periods of stillness.

4. An apparatus configured to receive information related to a sleep disorder in a subject, the apparatus comprising:
    one or more load cells configured for placement below one or more supports of a bed such that the bed and the one or more bed supports are physically supported by the load cells, the load cells further configured to convert force to an electrical signal indicative of the force; and
    a computing device coupled to at least one of the one or more load cells, the computing device comprising computer executable instructions for:
    receiving load cell signals from at least one of the one or more load cells;
    separately decimating the load cell signals and filtering the load cell signals to obtain downsampled load cell signal data and filtered load cell signal data, respectively;
    calculating a variance in the downsampled load cell signal data;
    calculating a normalized average power of the downsampled load cell signal data in a first frequency band;
    calculating a normalized average power of the downsampled load cell signal data in a second frequency band greater than the first frequency band;
    calculating a normalized average power of the downsampled load cell signal data in a third frequency band greater than the second frequency band;
    calculating a spectral entropy of the down-sampled load cell signal data;
    calculating a variance in the filtered load cell signal data;
    calculating a range of the filtered load cell signal data;
    calculating a respiration amplitude from the filtered load cell signal data; and
    applying a classifier to classify the load cell signals based on the variance in the downsampled load cell signal data, the normalized average power of the downsampled load cell signal data in the first frequency band, the normalized average power of the downsampled load cell signal data in the second frequency band, the normalized average power of the downsampled load cell signal data in the third frequency band, the spectral entropy of the down-sampled load cell signal data, the variance in the filtered load cell signal data, the range of the filtered load cell signal data, and the respiration amplitude from the filtered load cell signal data, the classifier differentiating between central apnea, hypopnea, and normal breathing; and identifying central apnea, hypopnea or normal breathing in the subject based on the classification of the load cell signal data.

5. The apparatus of claim 4, wherein the classifier is a Bayesian classifier in which parameters of the classifier are approximated using maximum likelihood probabilities of a training set of data which contains examples of sleep patterns of central apnea, hypopnea, and normal breathing.

6. The apparatus of claim 4, further including a transceiver coupled to the computing device or to at least one of the one or more load cells.

7. The apparatus of claim 4, further comprising an alarm, wherein the identifying central apnea, hpopnea, or normal breathing in the subject comprises identifying central apnea or hypopnea in the subject, and wherein the computer executable instructions are operable to actuate the alarm in response to the identifying central apnea or hypopnea in the subject.

8. The apparatus of claim 4, further including a support for a bed, the support configured to be added to the bed and tensioned for use with the one or more load cells.

9. The method of claim 1, wherein extracting features from the downsampled load cell signal data comprises:
 calculating a variance in the downsampled load cell signal data;
 calculating a normalized average power of the downsampled load cell signal data in a first frequency band;
 calculating a normalized average power of the downsampled load cell signal data in a second frequency band greater than the first frequency band;
 calculating a normalized average power of the downsampled load cell signal data in a third frequency band greater than the second frequency band; and
 calculating a spectral entropy of the down-sampled load cell signal data; and
 wherein extracting features from the filtered load cell signal data comprises:
 calculating a variance in the filtered load cell signal data;
 calculating a range of the filtered load cell signal data; and
 calculating a respiration amplitude from the filtered load cell signal data.

10. The method of claim 9, wherein the first frequency band comprises frequencies in an range of 0 Hz to 0.5 Hz, the second frequency band comprises frequencies in an approximate range of 0.6 Hz to 0.75 Hz, and the third frequency band comprises frequencies in an approximate range of 0.75 Hz to 5 Hz.

11. The method of claim 9, wherein for each frequency band, $[F_1, F_2]$, calculating the normalized average power of the downsampled load cell signal data in the frequency band comprises:
 multiplying the downsampled load cell signal data by a Blackman window to obtain a modified signal $x_B(t)$;
 calculating a power spectral density, $S(e^{j\omega})$, according to the equation:

$$S(e^{j\omega}) = \frac{1}{n}\left|\sum_{t=1}^{n} x_B(t)e^{-j\omega t}\right|^2;$$

and
 calculating an average power, P, according to the equation:

$$P = 2\sum_{i=F_1}^{F_2} S(f_i).$$

12. The method of claim 9, wherein
calculating the respiration amplitude from the filtered load cell signal data comprises:
 dividing the filtered load cell signal data into overlapping 5 second windows that have starting points offset by 0.1 seconds;
 for each window of the overlapping 5 second windows, calculating a range of the filtered load cell signal data in the window; and
 calculating a median of all the ranges.

13. The method of claim 1, wherein the load cells are placed beneath supports of the bed and tensioned to provide support and measure the load at a specific location.

14. The method of claim 9, wherein calculating the spectral entropy of the down-sampled load cell signal data comprises:
 calculating a power spectral density of the downsampled load cell signal data;
 segmenting the power spectral density into 100 equal frequency bins, f;
 normalizing an average power of each frequency bin to obtain a probability density, $p_f$, for each frequency bin; and
 calculating the spectral entropy, SE, according to the equation:

$$SE = \sum_{f=1}^{100} p_f \log_{10}\left(\frac{1}{p_f}\right).$$

* * * * *